US012351841B2

(12) United States Patent
Urbina et al.

(10) Patent No.: US 12,351,841 B2
(45) Date of Patent: Jul. 8, 2025

(54) AMYLASE ENZYMES

(71) Applicant: BASF SE, Ludwigshafen (DE)

(72) Inventors: Hugo Urbina, San Diego, CA (US); Asfia Qureshi, San Diego, CA (US); Adrienne Huston Davenport, Solana Beach, CA (US); Xuqiu Tan, San Diego, CA (US); Jochen Kutscher, Balzheim (DE); Andreas Funke, Dietenheim (DE); Michael Seitter, Voehringen (DE); Stefan Haefner, Speyer (DE); Anh-Huy Phan Le, San Diego, CA (US)

(73) Assignee: BASF SE, Ludwigshafen am Rhein (DE)

( * ) Notice: Subject to any disclaimer, the term of this patent is extended or adjusted under 35 U.S.C. 154(b) by 998 days.

(21) Appl. No.: 17/057,853

(22) PCT Filed: May 29, 2019

(86) PCT No.: PCT/EP2019/063896

§ 371 (c)(1),
(2) Date: Nov. 23, 2020

(87) PCT Pub. No.: WO2019/229101

PCT Pub. Date: Dec. 5, 2019

(65) Prior Publication Data

US 2021/0198643 A1 Jul. 1, 2021

Related U.S. Application Data

(60) Provisional application No. 62/677,451, filed on May 29, 2018.

(51) Int. Cl.

| | |
|---|---|
| ***C12N 9/28*** | (2006.01) |
| ***C11D 3/386*** | (2006.01) |
| ***C12N 9/26*** | (2006.01) |
| *A21D 8/04* | (2006.01) |

(52) U.S. Cl.

CPC ........ *C12N 9/2414* (2013.01); *C11D 3/38636* (2013.01); *C12N 9/2411* (2013.01); *C12N 9/2417* (2013.01); *C12Y 302/01001* (2013.01); *A21D 8/042* (2013.01)

(58) Field of Classification Search

CPC .................................................... C12N 9/2414

See application file for complete search history.

(56) References Cited

U.S. PATENT DOCUMENTS 8,222,035 B2 * 7/2012 Callen .................... A21D 8/042 435/254.2

FOREIGN PATENT DOCUMENTS

| | | | |
|---|---|---|---|
| CN | 104388449 | A | 3/2015 |
| EP | 2194133 | A2 | 6/2010 |
| WO | 02/068589 | A2 | 9/2002 |
| WO | 02/068597 | A2 | 9/2002 |
| WO | 03/083054 | A2 | 10/2003 |
| WO | 2004/042006 | A2 | 5/2004 |
| WO | WO-2004/111217 | A2 | 12/2004 |
| WO | 2008/080093 | A2 | 7/2008 |
| WO | 2013/116175 | A2 | 8/2013 |
| WO | 2017/106633 | A1 | 6/2017 |

OTHER PUBLICATIONS

Fransceus. J Ind Microbiol Biotechnol. May 2017;44(4-5):687-695.*

Sanavia. Computational and Structural Biotechnology Journal, vol. 18, 2020, pp. 1968-1979.*

Studer. Residue mutations and their impact on protein structure and function: detecting beneficial and pathogenic changes. Biochem. J. (2013) 449, 581-594.*

First Office Action from corresponding Chinese Application No. 201980043954.1 dated Sep. 13, 2023, and a brief English summary.

"SubName: Full=Alpha-amylase {EC0:0000313:EMBL:ASJ09798. 1}", Database UniProt [Online], XP002792743, Sep. 27, 2017, retrieved from EBI accession No. UNIPROT:A0A218PA76, 1 page.

"SubName: Full=Alpha-amylase {EC0:0000313:EMBL:BAA21130. 1}", Database UniProt [Online], XP002792742, Jan. 1, 1998, retrieved from EBI accession No. UNIPROT:033476, 1 page.

"SubName: Full=Alpha-amylase {ECO:0000313:EMBL:EEB73455. 2}", Database UniProt [Online], XP002792745, Feb. 10, 2009, retrieved from EBI accession No. UNIPROT:B7R3T4, 2 page.

"SubName: Full=Amylase {EC0:0000313 1lEMBL:AAB87860.1}; EC=3.2.1.1 {EC0:00003131EMBL:AAB87860.1}", Database UniProt [Online], XP002792741, Jun. 1, 1998, retrieved from EBI accession No. UNIPROT:050200, 1 page.

International Search Report for PCT Patent Application No. PCT/EP2019/063896, Issued on Jul. 24, 2019, 7 pages.

Jones, et al., "Amylase and 16S rRNA genes from a hyperthermophilic archaebacterium", Journal of Applied Microbiology, vol. 86, Issue 1, Jan. 1999, pp. 93-107.

Jones, et al., "Directed evolution of a maltogenic α-amylase from *Bacillus* sp. TS-25", Journal of Biotechnology, vol. 134, Issue 3-4, Apr. 30, 2008, pp. 325-333.

Kamon, et al., "Characterization and gene cloning of a maltotriose-forming exo-amylase from *Kitasatospora* sp. MK-1785", Applied Microbiology and Biotechnology, vol. 99, Issue 11, Jan. 27, 2015, pp. 4743-4753.

Mehta, et al., "Bacterial and Archaeal α-Amylases: Diversity and Amelioration of the Desirable Characteristics for Industrial Applications", Frontiers in Microbiology, vol. 7, Jul. 28, 2016, 21 pages.

(Continued)

*Primary Examiner* — Yong D Pak

(74) *Attorney, Agent, or Firm* — DLA Piper LLP (US)

(57) ABSTRACT

The present invention relates to variants of an alpha-amylase which have an increased exoamylase activity compared to the parent alpha-amylase. The present invention also relates to methods of making the variant alpha-amylase and the use of the variant alpha-amylase in baking, detergents, personal care products, in the processing of textiles, in pulp and paper processing, in the production of ethanol, lignocellulosic ethanol or syrups and as viscosity breaker in oilfield and mining industries.

12 Claims, 3 Drawing Sheets

Specification includes a Sequence Listing.

(56) References Cited

OTHER PUBLICATIONS

Tachibana, et al., "Cloning and expression of the α-amylase gene from the hyperthermophilic archaeon *Pyrococcus* sp. KOD1, and characterization of the enzyme", Journal of Fermentation and Bioengineering, vol. 82, Issue 3, 1996, pp. 224-232.
Lever, M., "A New Reaction for Colorimetric Determination of Carbohydrates", *Analytical Biochemistry*, 47, 273-279, 1972.
Smith, P.K. et al., "Measurement of Protein Using Bicinchonicic Acid", *Analytical Biochemistry*, 150, 76-85, 1985.
Fuwa, Hidetsugu, "A New Method for Microdetermination of Amylase Activity by the US of Amylose as the Substrate", *Journal of Biochemistry*, vol. 41, No. 5, 1954.
Needleman, Saul B., et al., "A General Method Applicable to the Search for Similarities in the Amino Acid Sequence of Two Proteins", *J. Mol. Biol*., 48, 443-453, 1970.

* cited by examiner

SEQUENCE LISTING

```
<160> NUMBER OF SEQ ID NOS: 2

<210> SEQ ID NO 1
<211> LENGTH: 436
<212> TYPE: PRT
<213> ORGANISM: Unknown
<220> FEATURE:
<223> OTHER INFORMATION: Synthetic Generated

<400> SEQUENCE: 1

Ala Lys Tyr Ser Glu Leu Glu Glu Gly Gly Val Ile Met Gln Ala Phe
1               5                   10                  15

Tyr Trp Asp Val Pro Gly Gly Gly Ile Trp Trp Asp Thr Ile Arg Gln
            20                  25                  30

Lys Ile Pro Glu Trp Tyr Asp Ala Gly Ile Ser Ala Ile Trp Ile Pro
        35                  40                  45

Pro Ala Ser Lys Gly Met Gly Gly Gly Tyr Ser Met Gly Tyr Asp Pro
    50                  55                  60

Tyr Asp Phe Phe Asp Leu Gly Glu Tyr Tyr Gln Lys Gly Thr Val Glu
65                  70                  75                  80

Thr Arg Phe Gly Ser Lys Glu Glu Leu Val Asn Met Ile Asn Thr Ala
                85                  90                  95

His Ser Tyr Gly Ile Lys Val Ile Ala Asp Ile Val Ile Asn His Arg
            100                 105                 110

Ala Gly Gly Asp Leu Glu Trp Asn Pro Phe Val Asn Asn Tyr Thr Trp
```

```
        115                 120                 125

Thr Asp Phe Ser Lys Val Ala Ser Gly Lys Tyr Thr Ala Asn Tyr Leu
    130                 135                 140

Asp Phe His Pro Asn Glu Val Lys Cys Cys Asp Glu Gly Thr Phe Gly
145                 150                 155                 160

Asp Phe Pro Asp Ile Ala His Glu Lys Ser Trp Asp Gln Tyr Trp Leu
                165                 170                 175

Trp Ala Ser Asn Glu Ser Tyr Ala Ala Tyr Leu Arg Ser Ile Gly Ile
            180                 185                 190

Asp Ala Trp Arg Phe Asp Tyr Val Lys Gly Tyr Gly Ala Trp Val Val
        195                 200                 205

Asn Asp Trp Leu Ser Trp Trp Gly Gly Trp Ala Val Gly Glu Tyr Trp
    210                 215                 220

Asp Thr Asn Val Asp Ala Leu Leu Asn Trp Ala Tyr Asp Ser Gly Ala
225                 230                 235                 240

Lys Val Phe Asp Phe Pro Leu Tyr Tyr Lys Met Asp Glu Ala Phe Asp
                245                 250                 255

Asn Thr Asn Ile Pro Ala Leu Val Tyr Ala Leu Gln Asn Gly Gly Thr
            260                 265                 270

Val Val Ser Arg Asp Pro Phe Lys Ala Val Thr Phe Val Ala Asn His
        275                 280                 285

Asp Thr Asp Ile Ile Trp Asn Lys Tyr Pro Ala Tyr Ala Phe Ile Leu
    290                 295                 300

Thr Tyr Glu Gly Gln Pro Val Ile Phe Tyr Arg Asp Tyr Glu Glu Trp
305                 310                 315                 320

Leu Asn Lys Asp Lys Leu Asn Asn Leu Ile Trp Ile His Glu His Leu
                325                 330                 335

Ala Gly Gly Ser Thr Lys Ile Leu Tyr Tyr Asp Asn Asp Glu Leu Ile
            340                 345                 350

Phe Met Arg Glu Gly Tyr Gly Ser Lys Pro Gly Leu Ile Thr Tyr Ile
        355                 360                 365

Asn Leu Gly Asn Asp Trp Ala Glu Arg Trp Val Asn Val Gly Ser Lys
    370                 375                 380

Phe Ala Gly Tyr Thr Ile His Glu Tyr Thr Gly Asn Leu Gly Gly Trp
385                 390                 395                 400

Val Asp Arg Trp Val Gln Tyr Asp Gly Trp Val Lys Leu Thr Ala Pro
                405                 410                 415

Pro His Asp Pro Ala Asn Gly Tyr Tyr Gly Tyr Ser Val Trp Ser Tyr
            420                 425                 430

Ala Gly Val Gly
        435


<210> SEQ ID NO 2
<211> LENGTH: 1311
<212> TYPE: DNA
<213> ORGANISM: Unknown
<220> FEATURE:
<223> OTHER INFORMATION: Synthetic Generated

<400> SEQUENCE: 2

gcaaagtact ccgaattgga ggaaggtggt gtaattatgc aagcctttta ctgggacgtt      60

cctggaggtg gaatttggtg ggataccatt agacagaaga tcccagaatg gtatgacgcc     120

ggtatttccg ctatctggat acctcctgcc tctaagggta tgggtggtgg ttactctatg     180

ggttatgacc catacgattt cttcgatttg ggagaatatt accagaaggg taccgtagaa     240
```

-continued

```
acaagatttg gttctaagga ggagcttgtt aacatgatta acactgctca ttcttacgga    300

attaaggtga ttgcagacat agtgatcaac catcgtgctg gtggagacct tgagtggaat    360

ccatttgtga ataactacac atggactgat tttcaaagg ttgcctccgg taaatatacc     420

gccaattacc ttgactttca cccaaatgag gtgaagtgtt gtgatgaagg tactttcggt    480

gattttcctg acatcgctca tgagaagtca tgggaccaat attggctgtg ggcatccaac    540

gaatcatacg ccgcttacct tagatcaatt ggtatcgatg cctggagatt tgattatgtg    600

aagggatatg gtgcatgggt tgttaatgat tggctgtctt ggtggggtgg ttgggccgtt    660

ggtgagtact gggacacaaa cgtggatgcc cttttgaact gggcatatga ttctggagct    720

aaagtgtttg acttcccctt gtactataag atggacgagg cttttgataa tactaacata    780

cccgctcttg tgtacgctct tcagaacgga ggtactgttg tttctagaga cccatttaag    840

gctgtgactt ttgttgcaaa ccatgacact gatatcatat ggaacaagta cccagcttat    900

gcattcattt tgacatacga gggacaacct gttattttct atagagacta tgaagaatgg    960

ttgaacaaag acaaattgaa taacctgatt tggattcatg aacatctggc tggtggttct   1020

accaaaattc tttactacga caatgacgaa ctgatattca tgcgtgaagg ttacggatcc   1080

aagcccggat tgattactta tatcaatctt ggaaacgact gggcagagag atgggtgaat   1140

gttggttcca agttcgccgg ttatacaatt cacgaataca ccggaaattt gggtggttgg   1200

gtagataggt gggtccaata tgacggttgg gttaagctta ctgctcctcc tcacgatccc   1260

gctaatggtt actatggata ctctgtgtgg tcttacgcag gtgtaggtta a            1311
```

AMYLASE ENZYMES

SEQUENCE LISTING

This application includes a nucleotide and amino acid sequence listing in computer readable form (CRF) as an ASC II text (.txt) file according to "Standard for the Presentation of Nucleotide and Amino Acid Sequence Listings in International Patent Applications Under the Patent Cooperation Treaty (PCT)" ST.25. The sequence listing is identified below and is hereby incorporated by reference into the specification of this application in its entirety and for all purposes.

| File Name | Date of Creation | Size |
|---|---|---|
| 161160-SequenceListing_ST25.txt | May 22, 2018 | 5.65 KB (5,786 bytes) |

FIELD OF THE INVENTION

The present invention relates to variants of an alpha-amylase which have an increased exoamylase activity compared to the parent alpha-amylase. The present invention also relates to methods of making the variant alpha-amylase and the use of the variant alpha-amylase in baking, detergents, personal care products, in the processing of textiles, in pulp and paper processing, in the production of ethanol, lignocellulosic ethanol or syrups and as viscosity breaker in oilfield and mining industries.

BACKGROUND OF THE INVENTION

Bread has been a staple of human nutrition for thousands of years. Bread is usually made by combining a flour, water, salt, yeast, and/or other food additives to make a dough or paste; then the dough is baked to make bread. Enzymes are known to be useful in baking because the enzymes' effects on the baking process may be similar or better than the effects of the chemical alternatives. Several different enzymes may be used for making bread, for example amylase enzymes have been known to help maintain freshness over time (anti-staling or hardness) and maintain resilience overtime. The staling of bread is caused by the cyrstallization of amylopectin which takes place in starch granules after baking. When bread stales, it loses softness and moisture of the crumbs which become less elastic.

Hence, there is still a need for an amylase that may provide fresh bread over a longer time than what is currently available or an amylase enzyme that may provide bread that is better than fresh over time.

One solution to this problem are the variant polypeptides having alpha-amylase enzyme activity that meet or exceed these industrial requirements. In addition, the alpha-amylase variants may be used in animal feed, detergents, personal care products, processing of textiles, pulp and paper processing, in the production of ethanol, in the production lignocellulosic ethanol, in the production of syrups, or as viscosity breakers in oilfield and mining industries.

SUMMARY OF THE INVENTION

The present inventors have surprisingly found that introducing amino acid modifications in the amino acid sequence of an alpha-amylase increases the exoamylase activity of the variant compared to the activity of the parent enzyme.

Accordingly, the present invention relates to a variant polypeptide of the alpha-amylase according to SEQ ID No. 1, comprising an amino acid sequence which is at least 80% identical to the sequence according to SEQ ID No. 1 and having alpha-amylase activity, wherein the variant polypeptide has an increased exoamylase activity compared to the alpha-amylase according to SEQ ID No. 1.

In one embodiment the variant comprises at least one amino acid modification compared to the amino acid sequence according to SEQ ID No. 1 which may be an amino acid substitution.

In one embodiment the at least one amino acid modification is at an amino acid residue position number selected from the group consisting of: 2, 3, 4, 21, 22, 25, 26, 29, 32, 35, 45, 53, 59, 68, 76, 82, 88, 90, 91, 96, 105, 117, 126, 128, 134, 141, 152, 160, 175, 197, 200, 234, 236, 243, 256, 257, 258, 261, 264, 270, 292, 311, 380, 416, 423, 433 and 435 in the numbering of SEQ ID No. 1.

In one embodiment the at least one amino acid modification is an amino acid substitution selected from the group consisting of: K2H, Y3R, S4T, P21E, P21W, G22Q, 125W, W26G, T29G, Q32R, P35K, 145M, G53A, S59P, F68P, K76R, R82N, E88Y, V90G, V90M, N91T, A96T, A105W, L117R, Y126V, W128Y, V134A, A141T, K152M, G160E, G160V, W175N, F197A, F197K, V200S, W234C, Y236H, F243A, F243K, F243T, D256A, N257R, T258C, P261C, P261F, V264R, G270Y, 1292A, 1292E, V311L, N380L, G416Q, G423M, A433W and V435S in the numbering of SEQ ID No. 1.

In one embodiment the variant polypeptide comprises a combination of amino acid modifications compared to the amino acid sequence according to SEQ ID No. 1.

The combination of amino acid modifications is a combination of amino acid substitutions may be selected from the group consisting of:

a. G22Q, P35K, S59P, W128Y, D256A;
b. G22Q, W128Y, W175N, V200S, A433W;
c. G22Q, P35K, S59P, D256A;
d. G22Q, W175N, V200S, D256A, A433W;
e. W128Y, W175N, D256A;
f. G22Q, S59P, V200S, D256A, A433W;
g. G22Q, W175N, V200S, D256A;
h. G22Q, S59P;
i. G22Q, P35K, W128Y, W175N, V200S, D256A, A433W;
j. G22Q, P35K, S59P, W128Y, A433W;
k. G22Q, W128Y, W175N, D256A;
l. P35K, W128Y, V200S, D256A;
m. G22Q, S59P, W175N, V200S, A433W;
n. G22Q, S59P, W128Y, V200S, A433W;
o. G22Q, S59P, W175N, V200S, D256A, A433W;
p. G22Q, S59P, W128Y, D256A;
q. S59P, V200S, D256A, A433W;
r. P35K, S59P, W128Y, W175N, V200S, D256A, A433W;
s. G22Q, S59P, W128Y, D256A, A433W;
t. G22Q, S59P, W128Y, W175N, V200S, 433W;
u. G22Q, W128Y, W175N, A433W;
v. S59P, W128Y, V200S;
w. P35K, S59P, V200S, A433W;
x. S59P, W128Y, V200S, D256A;
y. S59P, W128Y, V200S, A433W; and
z. W128Y, V200S, A433W in the numbering of SEQ ID No. 1.

In one embodiment the variant polypeptide is a fragment of the full length amino acid sequence.

In one embodiment the variant polypeptide comprises a hybrid of said at least one variant polypeptide and a second polypeptide having amylase activity, wherein the hybrid has alpha-amylase activity.

The present invention also relates to a composition comprising said variant polypeptide.

The composition may further comprise a second enzyme and the second enzyme may be selected from the group consisting of: a second alpha-amylase, a lipase, a beta-amylase, a G4-amylase, a xylanase, a protease, a cellulase, a glucoamylase, an oxidoreductase, a phospholipase, and a cyclodextrin glucanotransferase.

The present invention also relates to a method of making a variant polypeptide comprising: providing a template nucleic acid sequence encoding said polypeptide variant, transforming the template nucleic acid sequence into an expression host, cultivating the expression host to produce the variant polypeptide, and purifying the variant polypeptide.

In one embodiment the template nucleic acid is a variant nucleotide of the nucleic acid sequence as set forth in SEQ ID NO. 2, wherein the variant nucleotide is a nucleic acid sequence that is at least 80% identical to the nucleic acid sequence as set forth in SEQ ID No. 2, wherein the variant nucleotide encodes a polypeptide having alpha-amylase activity and having an increased exoamylase activity compared to the alpha-amylase encoded by the nucleic acid sequence according to SEQ ID No.2.

In one embodiment the expression host is selected from the group consisting of: a bacterial expression system, a yeast expression system, a fungal expression system, and a synthetic expression system.

The bacterial expression system may be selected from an *E. coli*, a *Bacillus*, a *Pseudomonas*, and a *Streptomyces*.

The yeast expression system may be selected from a *Candida*, a *Pichia*, a *Saccharomyces*, a *Schizosaccharomyces*.

The fungal expression system may be selected from a *Penicillium*, an *Aspergillus*, a *Fusarium*, a *Thermothelomyces*, a *Rhizomucor*, a *Rhizopus*, a *Thermomyces*, and a *Trichoderma*.

The present invention further relates to a method of preparing a dough or a baked product prepared from the dough, the method comprising adding a variant polypeptide as described herein to the dough and eventually baking the dough.

The present invention further relates to the use of said variant polypeptide for processing starch, for cleaning or washing textiles, hard surfaces, or dishes, for making ethanol, for treating an oil well, for processing pulp or paper, for feeding an animal or for making syrup.

In one embodiment, the use is a method for processing starch comprising, providing a starch, providing said variant polypeptide, contacting the starch and the variant polypeptide, wherein the polypeptide hydrolyses the starch. In one embodiment, the use is a method for processing starch comprising, providing a starch, providing said variant polypeptide, contacting the starch and the variant polypeptide, wherein the polypeptide hydrolyses the starch.

DETAILED DESCRIPTION OF THE INVENTION

Figure 1:
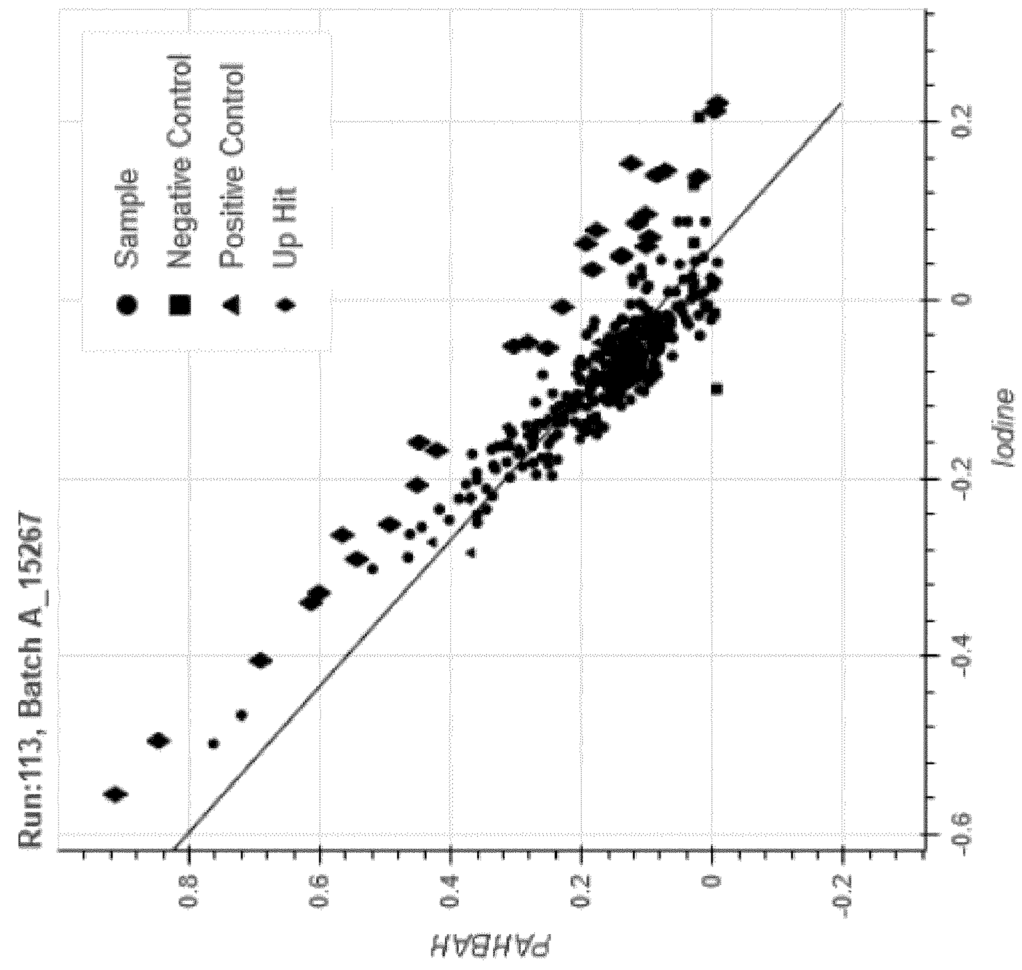
FIG. 1: Sample graph demonstrating the linear relationship between PAHBAH and Iodine assay values. The line is the line calculated based on the sample points. Black circles represent samples that fall along the linear regression line and are within the 90% confidence band (threshold). Black diamonds represent mutants that break the linear relationship and were identified as an "up hit".
Figure 2O:
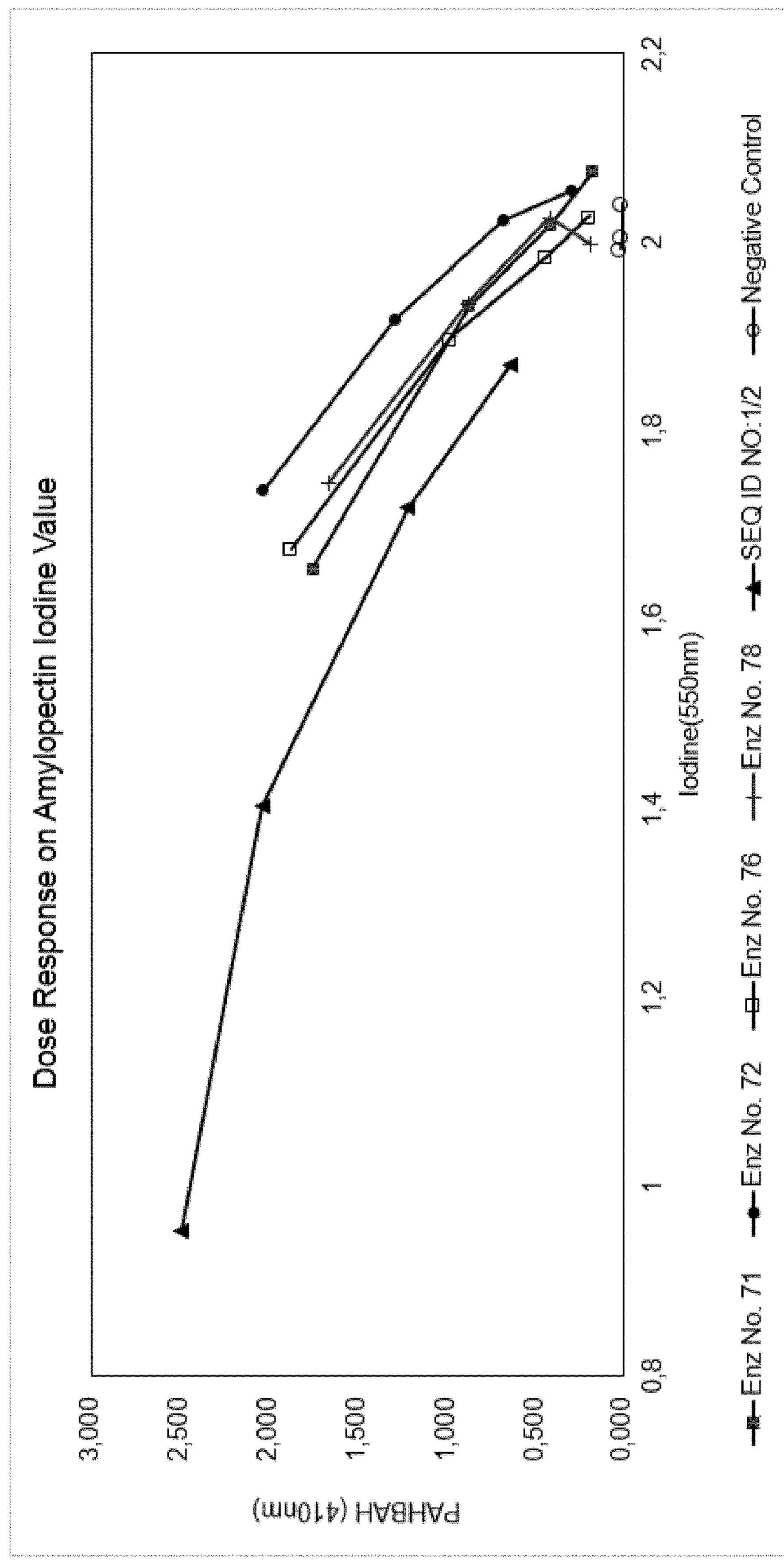
FIG. 2: Dose response on amylopectin as measured by PAHBAH and iodine assay of four different variant enzymes (Enzyme 71, 72, 76, and 78) as well as of the parent alpha-amylase (SEQ ID NO:1/2), and the negative control.

Although the present invention will be described with respect to particular embodiments, this description is not to be construed in a limiting sense.

Before describing in detail exemplary embodiments of the present invention, definitions important for understanding the present invention are given. Unless stated otherwise or apparent from the nature of the definition, the definitions apply to all methods and uses described herein.

As used in this specification and in the appended claims, the singular forms of "a" and "an" also include the respective plurals unless the context clearly dictates otherwise. In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%.

It is to be understood that the term "comprising" is not limiting. For the purposes of the present invention the term "consisting of" is considered to be a preferred embodiment of the term "comprising". If hereinafter a group is defined to comprise at least a certain number of embodiments, this is meant to also encompass a group which preferably consists of these embodiments only.

Furthermore, the terms "first", "second", "third" or "(a)", "(b)", "(c)", "(d)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. In case the terms "first", "second", "third" or "(a)", "(b)", "(c)", "(d)", "i", "ii" etc. relate to steps of a method or use or assay there is no time or time interval coherence between the steps, i.e. the steps may be carried out simultaneously or there may be time intervals of seconds, minutes, hours, days, weeks, months or even years between such steps, unless otherwise indicated in the application as set forth herein above or below.

It is to be understood that this invention is not limited to the particular methodology, protocols, reagents etc. described herein as these may vary. It is also to be understood that the terminology used herein is for the purpose of describing particular embodiments only, and is not intended to limit the scope of the present invention that will be limited only by the appended claims. Unless defined otherwise, all technical and scientific terms used herein have the same meanings as commonly understood by one of ordinary skill in the art.

As discussed above, the present invention is based on the finding that variants of an alpha-amylase have an increased exoamylase activity compared to the parent alpha-amylase. In baking applications the exoamylase activity is preferred, as it accomplishes the degradation of starch that leads to an anti-staling effect, but does not negatively affect the quality of the final baked product. In contrast, endoamylase activity can negatively affect the quality of the final baked product, as it leads to an accumulation of branched dextrins which for example lead to the production of a sticky or gummy bread crumb.

A "variant polypeptide" refers to an enzyme that differs from its parent polypeptide in its amino acid sequence. A "variant alpha-amylase" refers to an alpha-amylase that differs from its parent alpha-amylase in its amino acid sequence and has alpha-amylase activity. Variant polypeptides are described using the nomenclature and abbreviations for single amino acid molecules according to the recommendations of IUPAC for single letter or three letter amino acid abbreviations.

A "parent" polypeptide amino acid sequence is the starting sequence for introduction of amino acid modifications (e.g. by introducing one or more amino acid substitutions, insertions, deletions, or a combination thereof) to the sequence, resulting in "variants" of the parent polypeptide amino acid sequence. A parent polypeptide includes both a wild-type polypeptide amino acid sequence or a synthetically generated polypeptide amino acid sequence that is used as starting sequence for the introduction of (further) changes. Within the present invention the parent polypeptide is preferably the polypeptide having the amino acid sequence according to SEQ ID No. 1. Alternatively, the parent polypeptide may be a polypeptide comprising an amino acid sequence which is at least 90% identical to the amino acid sequence according to SEQ ID No. 1 and which does not have an amino acid modification at any of the following amino acid residues: 2, 3, 4, 21, 22, 25, 26, 29, 32, 35, 45, 53, 59, 68, 76, 82, 88, 90, 91, 96, 105, 117, 126, 128, 134, 141, 152, 160, 175, 197, 200, 234, 236, 243, 256, 257, 258, 261, 264, 270, 292, 311, 380, 416, 423, 433 and 435 compared to the sequence according to SEQ ID No. 1.

Alpha-amylases (EC 3.2.1.1) are enzymes which hydrolyze (1->4)-alpha-D-glucosidic linkages in polysaccharides containing three or more (1->4)-alpha-linked D-glucose units, such as starch, amylopectin and amylose polymers. The hydrolysis of starch by an alpha-amylase can reduce crystallization, as the length of the amylopectin side chains is reduced, and increase anti-staling in baking processes. Alpha-amylases are widely used in the initial stages of starch processing, in wet corn milling, in alcohol production, as cleaning agents in detergent matrices, in the textile industry, in baking applications, in the beverage industry, in oilfield in drilling processes and in animal feed.

Alpha-amylases have been isolated from plants, animals and microbial sources, wherein the alpha-amylases from bacteria are most widely used. Such bacterial alpha-amylases include those from *Bacillus stearothermophilus, Bacillus subtilis, Bacillus licheniformis* and *Bacillus amyloliquefaciens*. In addition, amylase enzymes are disclosed in the following patent applications: WO 02/068589, WO 02/068597, WO 03/083054, WO 04/042006, WO 08/080093, WO 2013/116175, and WO 2017/106633.

Commercial amylase enzymes used in food processing and baking include: Veron® available from AB Enzymes; BakeDream®, BakeZyme®, and Panamore® available from DSM; POWERSoft®, Max-LIFE™, POWERFlex®, and POWERFresh® available from DuPont; and Fungamyl®, Novamyl®, OptiCake®, and Sensea® available from Novozymes.

The alpha-amylase activity can be determined by various assays known to the person skilled in the art, including the BCA Reducing Ends Assay (Smith, P. K. (1985) Anal. Biochem. 150 (1): 76-85), PAHBAH assay (Lever M. (1972) Anal. Biochem. 47: 273-279), the iodine assay (Fuwa (1954) J. Biochem. 41: 583-603), Phadebas assay (available e.g. from Magic Life Sciences) and the starch plate assay.

The variant polypeptides of the present invention are characterized in that they have an increased exoamylase activity compared to the parent polypeptide, preferably compared to the polypeptide with the amino acid sequence according to SEQ ID No. 1. The term "exoamylase activity" is intended to mean the cleavage of a starch molecule from the non-reducing end of the substrate. In contrast, "endoamylase activity" means that α-D-(1->4)-O-glucosidic linkages within the starch molecule are cleaved in a random fashion.

Preferably, an increased exoamylase activity can be determined by measuring the degradation of amylopectin using different concentrations of both the variant polypeptide and the parent polypeptide and determining amylopectin degradation by both the iodine and the PAHBAH assay for each of the different concentrations of the variant and parent polypeptides. Then a curve is established by using the PAHBAH and iodine values for each concentration of the alpha-amylases tested. A variant polypeptide is considered to show an increased exoamylase activity, if for a given PAHBAH value the iodine value is higher than for the parent polypeptide. An example of such a determination is provided in the examples section herein.

"Sequence Identity", "% sequence identity", "% identity", "% identical" or "sequence alignment" means a comparison of a first amino acid sequence to a second amino acid sequence, or a comparison of a first nucleic acid sequence to a second nucleic acid sequence and is calculated as a percentage based on the comparison. The result of this calculation can be described as "percent identical" or "percent ID."

Generally, a sequence alignment can be used to calculate the sequence identity by one of two different approaches. In the first approach, both mismatches at a single position and gaps at a single position are counted as non-identical positions in final sequence identity calculation.

In the second approach, mismatches at a single position are counted as non-identical positions in final sequence identity calculation; however, gaps at a single position are not counted (ignored) as non-identical positions in final sequence identity calculation. In other words, in the second approach gaps are ignored in final sequence identity calculation. The difference between these two approaches, i.e. counting gaps as non-identical positions vs ignoring gaps, at a single position can lead to variability in the sequence identity value between two sequences.

A sequence identity is determined by a program, which produces an alignment, and calculates identity counting both mismatches at a single position and gaps at a single position as non-identical positions in final sequence identity calculation. For example program Needle (EMBOS), which has implemented the algorithm of Needleman and Wunsch (Needleman and Wunsch, 1970, J. Mol. Biol. 48: 443-453), and which calculates sequence identity per default settings by first producing an alignment between a first sequence and a second sequence, then counting the number of identical positions over the length of the alignment, then dividing the number of identical residues by the length of an alignment, then multiplying this number by 100 to generate the % sequence identity [% sequence identity=(# of Identical residues/length of alignment)×100)].

A sequence identity can be calculated from a pairwise alignment showing both sequences over the full length, so showing the first sequence and the second sequence in their full length ("Global sequence identity"). For example, program Needle (EMBOSS) produces such alignments; % sequence identity=(# of identical residues/length of alignment)×100)].

A sequence identity can be calculated from a pairwise alignment showing only a local region of the first sequence or the second sequence ("Local Identity"). For example, program Blast (NCBI) produces such alignments; % sequence identity=(# of Identical residues/length of alignment)×100)].

The sequence alignment is preferably generated by using the algorithm of Needleman and Wunsch (J. Mol. Biol. (1979) 48, p. 443-453). Preferably, the program "NEEDLE" (The European Molecular Biology Open Software Suite (EMBOSS)) is used with the programs default parameter (gap open=10.0, gap extend=0.5 and matrix=EBLOSUM62 for proteins and matrix=EDNAFULL for nucleotides). Then, a sequence identity can be calculated from the alignment showing both sequences over the full length, so showing the first sequence and the secand sequence in their full length ("Global sequence identity"). For example: % sequence identity=(# of identical residues/length of alignment)×100)].

The variant polypeptides are described by reference to an amino acid sequence which is at least n % identical to the amino acid sequence of the respective parent enzyme with "n" being an integer between 80 and 100. The variant polypeptides include enzymes that are at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identical when compared to the full length amino acid sequence of the parent alpha-amylase according to SEQ ID No. 1, wherein the enzyme variant has alpha-amylase activity and an increased exoamylase activity compared to the parent polypeptide according to SEQ ID No. 1.

The variant polypeptide comprises at least one amino acid modification compared to the parent polypeptide, preferably the polypeptide according to SEQ ID No. 1. The term "amino acid modification" means that the amino acid sequence of the variant polypeptide is modified compared to the amino acid sequence of the parent polypeptide, preferably the polypeptide according to SEQ ID No. 1. The term "amino acid modification" is not intended to comprise modifications to an amino acid residue itself, such as, but not limited to, phosphorylation, myristoylation, palmitoylation, isoprenylation, acetylation, alkylation, amidation, gamma-carboxylation or glycoslation. The term "amino acid modification" includes amino acid substitution, amino acid insertion and amino acid deletion. Hence, the variant polypeptide of the present invention comprises at least one amino acid substitution, amino acid insertion and/or amino acid deletion compared to the parent polypeptide, preferably the polypeptide according to SEQ ID No. 1. Preferably, the at least one amino acid modification is at least one amino acid substitution.

"Amino acid substitutions" are described by providing the original amino acid residue in the parent polypeptide followed by the number of the position of this amino acid residue within the amino acid sequence. For example, a substitution of amino acid residue 22 means that the amino acid of the parent at position 22 can be substituted with any of the 19 other amino acid residues and is designated as G22. In addition, a substitution can be described by providing the original amino acid residue in the parent polypeptide followed by the number of the position of this amino acid residue within the amino acid sequence and followed by the specific substituted amino acid within the variant polypeptide. For example, the substitution of glycine at position 22 with glutamine is designated as "Gly22Gln" or "G22Q". Combinations of substitutions, are described by inserting comas between the amino acid residues, for example: G22Q, P35K, S59P, W128Y, D256A; represent a combination of substitutions of five different amino acid residues when compared to a parent polypeptide. Variants having a substitution on the amino acid level are encoded by a nucleic acid sequence which differs from the parent nucleic acid sequence encoding the parent polypeptide at least in the position encoding the substituted amino acid residue.

The amino acid substitution in the variant polypeptide may be a conservative amino acid substitution. A "conservative amino acid substitution" or "substitution with a related amino acid" means replacement of one amino acid residue in an amino acid sequence with a different amino acid residue having a similar property at the same position compared to the parent amino acid sequence. Some examples of a conservative amino acid substitution include, but are not limited to, replacing a positively charged amino acid residue with a different positively charged amino acid residue; replacing a polar amino acid residue with a different polar amino acid residue; replacing a non-polar amino acid residue with a different non-polar amino acid residue, replacing a basic amino acid residue with a different basic amino acid residue, or replacing an aromatic amino acid residue with a different aromatic amino acid residue.

A list of conservative amino acid substitutions is provided in the Table below (see for example Creighton (1984) Proteins. W.H. Freeman and Company (Eds)).

| Residue | Conservative Substitution(s) |
|---|---|
| Ala | Ser |
| Arg | Lys |
| Asn | Gln, His |
| Asp | Glu |
| Gln | Asn |
| Cys | Ser |
| Glu | Asp |
| Gly | Pro |
| His | Asn, Gln |
| Ile | Leu, Val |
| Leu | Ile, Val |
| Lys | Arg, Gln |
| Met | Leu, Ile |
| Phe | Met, Leu, Tyr |
| Ser | Thr, Gly |
| Thr | Ser, Val |
| Trp | Tyr |
| Tyr | Trp, Phe |
| Val | Ile, Leu |

An "amino acid insertion" is described by providing the number of the position within the amino acid sequence behind which the amino acid is inserted followed by an apostrophe and the specific inserted amino acid residue. For example, the insertion of serine behind position 84 is designated as "84'S". Variants having an insertion on the amino acid level are encoded by a nucleic acid sequence which differs from the parent nucleic acid sequence encoding the parent polypeptide at least in the position encoding the inserted amino acid residue.

An "amino acid deletion" is described by providing the number of the position within the amino acid sequence at which the amino acid residue is deleted followed by a delta and the specific deleted amino acid residue. For example, the deletion of glycine on position 10 is designated as "10ΔG". Variants having deletions on the amino acid level are encoded by a nucleic acid sequence which differs from the parent nucleic acid sequence encoding the parent polypeptide at least at the position encoding the deleted amino acid residue.

In one embodiment the variant polypeptide comprises at least one amino acid modification at an amino acid residue position number selected from the group consisting of: 2, 3, 4, 21, 22, 25, 26, 29, 32, 35, 45, 53, 59, 68, 76, 82, 88, 90, 91, 96, 105, 117, 126, 128, 134, 141, 152, 160, 175, 197, 200, 234, 236, 243, 256, 257, 258, 261, 264, 270, 292, 311, 380, 416, 423, 433 and 435 in the numbering of SEQ ID No. 1.

Preferably, the variant polypeptide comprises at least one amino acid substitution at an amino acid residue position number selected from the group consisting of: 2, 3, 4, 21, 22, 25, 26, 29, 32, 35, 45, 53, 59, 68, 76, 82, 88, 90, 91, 96, 105, 117, 126, 128, 134, 141, 152, 160, 175, 197, 200, 234, 236, 243, 256, 257, 258, 261, 264, 270, 292, 311, 380, 416, 423, 433 and 435 in the numbering of SEQ ID No. 1.

In one embodiment the variant polypeptide comprises at least one amino acid modification at an amino acid residue position number selected from the group consisting of: 2, 3, 4, 21, 22, 25, 26, 29, 32, 45, 68, 76, 82, 88, 91, 96, 117, 126, 128, 134, 141, 160, 175, 197, 200, 234, 236, 243, 256, 257, 258, 261, 264, 292, 311, 380, 416, 423, 433 and 435 in the numbering of SEQ ID No. 1.

Preferably, the variant polypeptide comprises at least one amino acid substitution at an amino acid residue position number selected from the group consisting of: 2, 3, 4, 21, 22, 25, 26, 29, 32, 45, 68, 76, 82, 88, 91, 96, 117, 126, 128, 134, 141, 160, 175, 197, 200, 234, 236, 243, 256, 257, 258, 261, 264, 292, 311, 380, 416, 423, 433 and 435 in the numbering of SEQ ID No. 1.

In one embodiment the variant polypeptide comprises at least one amino acid modification at an amino acid residue position number selected from the group consisting of: 35, 59, 128, 175, 200, 256 and 433.

Preferably, the variant polypeptide comprises at least one amino acid substitution at an amino acid residue position number selected from the group consisting of: 35, 59, 128, 175, 200, 256 and 433.

Also preferably, the at least one amino acid substitution is selected from the group consisting of: K2H, Y3R, S4T, P21E, P21W, G22Q, 125W, W26G, T29G, Q32R, P35K, 145M, G53A, S59P, F68P, K76R, R82N, E88Y, V90G, V90M, N91T, A96T, A105W, L117R, Y126V, W128Y, V134A, A141T, K152M, G160E, G160V, W175N, F197A, F197K, V200S, W234C, Y236H, F243A, F243K, F243T, D256A, N257R, T258C, P261C, P261F, V264R, G270Y, 1292A, 1292E, V311L, N380L, G416Q, G423M, A433W and V435S in the numbering of SEQ ID No. 1.

Also preferably, the at least one amino acid substitution is selected from the group consisting of: K2H, Y3R, S4T, P21E, P21W, G22Q, 125W, W26G, T29G, Q32R, 145M, F68P, K76R, R82N, E88Y, N91T, A96T, L117R, W128Y, V134A, A141T, G160E, G160V, W175N, F197A, F197K, V200S, W234C, Y236H, F243A, F243K, F243T, D256A, N257R, T258C, P261C, P261F, V264R, 1292E, V311L, N380L, G416Q, G423M, A433W and V435S in the numbering of SEQ ID No. 1.

More preferably, the at least one amino acid substitution is selected from the group consisting of: P35K, S59P, W128Y, W175N, V200S, D256A and A433W in the numbering of SEQ ID No. 1.

The variant polypeptide may comprise a combination of amino acid modifications compared to the amino acid sequence of the parent polypeptide, preferably compared to the amino acid sequence according to SEQ ID No. 1. The variant polypeptide may comprise a combination of amino acid substitutions compared to the amino acid sequence of the parent polypeptide, preferably compared to the amino acid sequence according to SEQ ID No. 1.

Preferably, the combination of amino acid modifications comprises at least two, at least three, at least four, at least five or at least six amino acid modifications at amino acid residue position numbers selected from the group consisting of: 2, 3, 4, 21, 22, 25, 26, 29, 32, 35, 45, 53, 59, 68, 76, 82, 88, 90, 91, 96, 105, 117, 126, 128, 134, 141, 152, 160, 175, 197, 200, 234, 236, 243, 256, 257, 258, 261, 264, 270, 292, 311, 380, 416, 423, 433 and 435 in the numbering of SEQ ID No. 1.

Also preferably, the combination of amino acid modifications comprises at least two, at least three, at least four, at least five or at least six amino acid substitutions at amino acid residue position numbers selected from the group consisting of: 2, 3, 4, 21, 22, 25, 26, 29, 32, 35, 45, 53, 59, 68, 76, 82, 88, 90, 91, 96, 105, 117, 126, 128, 134, 141, 152, 160, 175, 197, 200, 234, 236, 243, 256, 257, 258, 261, 264, 270, 292, 311, 380, 416, 423, 433 and 435 in the numbering of SEQ ID No. 1.

More preferably, the combination of amino acid modifications comprises at least two, at least three, at least four, at least five or at least six amino acid modifications at amino acid residue position numbers selected from the group consisting of: 35, 59, 128, 175, 200, 256 and 433 in the numbering of SEQ ID No. 1. Also more preferably, the combination of amino acid substitutions comprises at least two, at least three, at least four, at least five or at least six amino acid substitutions at amino acid residue position numbers selected from the group consisting of: 35, 59, 128, 175, 200, 256 and 433 in the numbering of SEQ ID No. 1.

Even more preferably, the combination of amino acid substitutions comprises at least two, at least three, at least four, at least five or at least six amino acid substitutions selected from the group consisting of: P35K, S59P, W128Y, W175N, V200S, D256A and A433W in the numbering of SEQ ID No. 1.

Particularly preferably, the combination of amino acid substitutions is selected from the group consisting of:

(a) G22Q, P35K, S59P, W128Y, D256A;
(b) G22Q, W128Y, W175N, V200S, A433W;
(c) G22Q, P35K, S59P, D256A;
(d) G22Q, W175N, V200S, D256A, A433W;
(e) W128Y, W175N, D256A;
(f) G22Q, S59P, V200S, D256A, A433W;
(g) G22Q, W175N, V200S, D256A;
(h) G22Q, S59P;
(i) G22Q, P35K, W128Y, W175N, V200S, D256A, A433W;
(j) G22Q, P35K, S59P, W128Y, A433W;
(k) G22Q, W128Y, W175N, D256A;
(l) P35K, W128Y, V200S, D256A;
(m) G22Q, S59P, W175N, V200S, A433W;
(n) G22Q, S59P, W128Y, V200S, A433W;
(o) G22Q, S59P, W175N, V200S, D256A, A433W;
(p) G22Q, S59P, W128Y, D256A;
(q) S59P, V200S, D256A, A433W;

(r) P35K, S59P, W128Y, W175N, V200S, D256A, A433W;
(s) G22Q, S59P, W128Y, D256A, A433W;
(t) G22Q, S59P, W128Y, W175N, V200S, 433W;
(u) G22Q, W128Y, W175N, A433W;
(v) S59P, W128Y, V200S;
(w) P35K, S59P, V200S, A433W;
(x) S59P, W128Y, V200S, D256A;
(y) S59P, W128Y, V200S, A433W; and
(z) W128Y, V200S, A433W in the numbering of SEQ ID No. 1.

Most preferably, the combination of amino acid substitutions is selected from the group consisting of:

(a) S59P, V200S, D256A, A433W;
(b) P35K, S59P, W128Y, W175N, V200S, D256A, A433W;
(c) S59P, W128Y, V200S; and
(d) S59P, W128Y, V200S, D256A in the numbering of SEQ I NO. 1.

A "fragment" of an alpha-amylase is understood to refer to a smaller part of the alpha-amylase which consists of a contiguous amino acid sequence found in the amino acid sequence of the alpha-amylase and which has alpha-amylase activity. The skilled person knows that for a fragment to be enzymatically active the fragment has to comprise at least the amino acids present in the catalytic centre of the alpha-amylase. These amino acids are either known for a given alpha-amylase or can easily be identified by the skilled person, for example by homology screening or mutagenesis. Preferably, the fragment of the alpha-amylase has an increased exoamylase activity compared to the full-length polypeptide according to SEQ ID No. 1. Preferably, the fragment comprises at least 70%, at least 80%, at least 85%, at least 90%, at least 95%, at least 96%, at least 97%, at least 98%, or at least 99% of the nucleotides of the full-length polypeptide according to SEQ ID No.1.

The variant polypeptide having alpha-amylase activity may be a hybrid of more than one alpha-amylase enzyme. A "hybrid" or "chimeric" or "fusion protein" means that a domain of a first variant polypeptide alpha-amylase is combined with a domain of a second alpha-amylase to form a hybrid amylase and the hybrid has alpha-amylase activity. Preferably, the hybrid alpha-amylase has an increased exoamylase activity compared to the polypeptide according to SEQ ID No. 1. A domain of variant polypeptides having alpha-amylase enzyme activity can be combined with a domain of a commercially available amylase, such as Veron® available from AB Enzymes; BakeDream®, BakeZyme®, and Panamore® available from DSM; POWERSoft®, Max-LIFE™, POWERFlex®, and POWERFresh® available from DuPont; and Fungamyl®, Novamyl®, OptiCake®, and Sensea® available from Novozymes. In addition, domains from various amylase enzymes can be recombined into a single enzyme, wherein the enzyme has alpha-amylase activity. Preferably, the hybrid alpha-amylase comprising domains from various amylase enzymes has an increased exoamylase activity compared to the polypeptide according to SEQ ID No. 1.

The variant polypeptides having alpha-amylase activity may be a "mature polypeptide." A mature polypeptide means an enzyme in its final form including any post-translational modifications, glycosylation, phosphorylation, truncation, N-terminal modifications, C-terminal modifications or signal sequence deletions. A mature polypeptide can vary depending upon the expression system, vector, promoter, and/or production process.

"Enzymatic activity" means at least one catalytic effect exerted by an enzyme. Enzymatic activity is expressed as units per milligram of enzyme (specific activity) or molecules of substrate transformed per minute per molecule of enzyme (molecular activity). Enzymatic activity can be specified by the enzymes actual function and within the present invention means alpha-amylase activity as described above.

Enzymatic activity changes during storage or operational use of the enzyme. The term "enzyme stability" relates to the retention of enzymatic activity as a function of time during storage or operation.

To determine and quantify changes in catalytic activity of enzymes stored or used under certain conditions over time, the "initial enzymatic activity" is measured under defined conditions at time zero (100%) and at a certain point in time later (x %). By comparison of the values measured, a potential loss of enzymatic activity can be determined in its extent. The extent of enzymatic activity loss determines the stability or non-stability of an enzyme.

Parameters influencing the enzymatic activity of an enzyme and/or storage stability and/or operational stability are for example pH, temperature, and presence of oxidative substances.

"pH stability", refers to the ability of a protein to function over a specific pH range. In general, most enzymes are working under conditions with rather high or rather low pH ranges.

The variant polypeptide may be active over a broad pH at any single point within the range from about pH 4.0 to about pH 12.0. The variant polypeptide having alpha-amylase activity is active over a range of pH 4.0 to pH 11.0, pH 4.0 to pH 10.0, pH 4.0 to pH 9.0, pH 4.0 to pH 8.0, pH 4.0 to pH 7.0, pH 4.0 to pH 6.0, or pH 4.0 to pH 5.0. The variant polypeptide having alpha-amylase enzyme activity is active at pH 4.0, pH 4.1, pH 4.2, pH 4.3, pH 4.4, pH 4.5, pH 4.6, pH 4.7, pH 4.8, pH 4.9, pH 5.0, pH 5.1, pH 5.2, pH 5.3, pH 5.4, pH 5.5, pH 5.6, pH 5.7, pH 5.8, pH 5.9, pH 6.0, pH 6.1, pH 6.2, pH 6.3, pH 6.4, pH 6.5, pH 6.6, pH 6.7, pH 6.8, pH 6.9, pH 7.0, pH 7.1, pH 7.2, pH 7.3, pH 7.4, pH 7.5, pH 7.6, pH 7.7, pH 7.8, pH 7.9, pH 8.0, pH 8.1, pH 8.2, pH 8.3, pH 8.4, pH 8.5, pH 8.6 pH 8.7, pH 8.8 pH 8.9, pH 9.0, pH 9.1, pH 9.2, pH 9.3, pH 9.4, pH 9.5, pH 9.6, pH 9.7, pH 9.8, pH 9.9, pH 10.0, pH 10.1, pH 10.2, pH 10.3, pH 10.4, pH 10.5, pH 10.6, pH 10.7, pH 10.8, pH 10.9, pH 11.0, pH 11.1, pH 11.2, pH 11.3, pH 11.4, pH 11.5, pH 11.6, pH 11.7, pH 11.8, pH 11.9, pH 12.0, pH 12.1, pH 12.2, pH 12.3, pH 12.4, and pH 12.5, pH 12.6, pH 12.7, pH 12.8, pH 12.9, and higher.

The terms "thermal stability" and "thermostability" refer to the ability of a protein to function over a temperature range. In general, most enzymes have a finite range of temperatures at which they function. In addition to enzymes that work at mid-range temperatures (e.g., room temperature), there are enzymes that are capable of working at very high or very low temperatures. Thermostability is characterized by what is known as the T50 value (also called half-life, see above). The T50 indicates the temperature at which 50% residual activity is still present after thermal inactivation for a certain time compared with a reference sample which has not under-gone thermal treatment.

The terms "thermal tolerance" and "thermotolerance" refer to the ability of a protein to function after exposure to a specific temperature, such as a very high or very low temperature. A thermotolerant protein may not function at the exposure temperature, but will function once returned to a favorable temperature.

Variant polypeptides may be active over a broad temperature used at any time during a baking process, wherein the temperature is any point in the range from about 20° C. to about 60° C. The variant polypeptides having alpha-amylase enzyme activity are active at a temperature range from 20° C. to 55° C., 20° C. to 50° C., 20° C. to 45° C., 20° C. to 40° C., 20° C. to 35° C., 20° C. to 30° C., or 20° C. to 25° C. The variant polypeptides having alpha-amylase enzyme activity are active at a temperature of at least 19° C., 20° C., 21° C., 22° C., 23° C., 24° C., 25° C., 26° C., 27° C., 28° C., 29° C., 30° C., 31° C. 32° C., 33° C., 34° C., 35° C., 36° C., 37° C., 38° C., 39° C., 40° C., 41° C. 42° C., 43° C., 44° C., 45° C., 46° C., 47° C., 48° C., 49° C., 50° C., 51° C. 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C. or higher temperatures.

Preferably, the variant alpha-amylase according to the present invention is a recombinant protein which is produced using bacteria, fungi, or yeast expression systems. "Expression system" also means a host microorganism, expression hosts, host cell, production organism, or production strain and each of these terms can be used interchangeably. Examples of expression systems include, but are not limited to: *Aspergillus niger, Aspergillus oryzae, Hansenula polymorpha, Thermomyces lanuginosus, Fusarium oxysporum, Fusarium heterosporum, Escherichia coli, Bacillus*, preferably *Bacillus subtilis* or *Bacillus licheniformis, Pseudomonas*, preferably *Pseudomonas fluorescens, Pichia pastoris* (also known as *Komagataella phaffii*), *Thermothelomyces thermophila* (previously known as *Myceliopthora thermophila* (C1)), *Schizosaccharomyces pombe, Trichoderma*, preferably *Trichoderma reesei* and *Saccharomyces*, preferably *Saccharomyces cerevisiae.*

The term "heterologous" (or exogenous or foreign or recombinant) polypeptide includes:

(a) a polypeptide that is not native to the host cell. The protein sequence of such a heterologous polypeptide is a synthetic, non-naturally occurring, "man made" protein sequence;

(b) a polypeptide native to the host cell in which structural modifications, e.g., deletions, substitutions, and/or insertions, have been made to alter the native polypeptide; or (c) a polypeptide native to the host cell whose expression is quantitatively altered, e.g. by using a stronger promoter, or whose expression is directed from a genomic location different from the native host cell as a result of manipulation of the DNA of the host cell by recombinant DNA techniques.

The term "heterologous" (or exogenous or foreign or recombinant) polynucleotide refers to:

(a) a polynucleotide that is not native to the host cell;

(b) a polynucleotide native to the host cell in which structural modifications, e.g., deletions, substitutions, and/or insertions, have been made to alter the native polynucleotide;

(c) a polynucleotide native to the host cell whose expression is quantitatively altered as a result of manipulation of the regulatory elements of the polynucleotide by recombinant DNA techniques, e.g., by using a stronger promoter; or (d) a polynucleotide native to the host cell, but integrated at a genomic locus other than its natural genomic locus as a result of genetic manipulation by recombinant DNA techniques.

With respect to two or more polynucleotide sequences or two or more amino acid sequences, the term "heterologous" is used to characterize that the two or more polynucleotide sequences or two or more amino acid sequences do not occur naturally in the specific combination with each other.

"Vector" means any kind of construct suitable to carry foreign polynucleotide sequences for transfer to another cell, or for stable or transient expression within a given cell. The term "vector" encompasses any kind of cloning vehicles, such as, but not limited to, plasmids, phagemids, viral vectors (e.g., phages), bacteriophage, baculoviruses, cosmids, fosmids, artificial chromosomes, or any other vectors specific for specific hosts of interest. Low copy number or high copy number vectors are also included. Foreign polynucleotide sequences usually comprise a coding sequence, which may be referred to as a "gene of interest." The gene of interest may comprise introns and exons, depending on the kind of origin or destination of host cell.

The present invention also includes a variant of the nucleic acid sequence as set forth in SEQ ID No. 2, wherein the variant nucleic acid sequence is a nucleic acid sequence that is at least 80% identical to the nucleic acid sequence as set forth in SEQ ID No. 2 and wherein the variant nucleic acid sequence encodes a variant polypeptide having alpha-amylase activity which has an increased exoamylase activity compared to the parent polypeptide, preferably the polypeptide encoded by the nucleic acid sequence according to SEQ ID No. 2 and/or the polypeptide having the amino acid sequence according to SEQ ID No. 1.

A method of making the variant polypeptides of the present invention comprises:

(a) providing a template nucleic acid sequence encoding a variant polypeptide having alpha-amylase activity;

(b) transforming the template nucleic acid sequence into an expression host; and (c) cultivating the expression host to produce the variant polypeptide, and purifying the variant polypeptide.

The template nucleic acid sequence is a variant of the nucleic acid sequence as set forth in SEQ ID No. 2, wherein the variant nucleic acid sequence is at least 80% identical to the nucleic acid sequence as set forth in SEQ ID No. 2 and wherein the variant nucleic acid sequence encodes a polypeptide having alpha-amylase activity and an increased exoamylase activity compared to the parent polypeptide, preferably the polypeptide according to SEQ ID No. 1.

The polypeptide variants having alpha-amylase enzyme activity may be used or formulated alone or as a mixture of enzymes.

The formulation containing the variant polypeptide of the present invention may be a solid form such as powder, a lyophilized preparation, a granule, a tablet, a bar, a crystal, a capsule, a pill, a pellet, or in a liquid form such as in an aqueous solution, an aerosol, a gel, a paste, a slurry, an aqueous/oil emulsion, a cream, a capsule, or in a vesicular or micellar suspension.

The variant polypeptide of the present invention may be used in combination with at least one other enzyme. The other enzyme may be from the same class of enzymes, for example, may be a second alpha-amylase. The other enzyme may also be from a different class of enzymes, for example may be a lipase. The combination with at least one other enzyme may be a composition comprising at least three enzymes. The three enzymes may be from the same class of enzymes, for example the combination may comprise the variant polypeptide of the present invention, a second amylase, and a third amylase; or the enzymes may be from different class of enzymes for example the combination may comprise the variant polypeptide of the present invention, a lipase, and a xylanase.

The second enzyme may be selected from the group consisting of: a second alpha-amylase, a beta-amylase, a glucan 1, 4-alpha-maltotetraohydrolase, also known as exomaltotetraohydrolase, G4-amylase; a glucan 1,4-alpha-maltohydrolase, also known as maltogenic alpha-amylase, a cyclodextrin glucanotransferase, a glucoamylase; an endo-1,4-beta-xylanase; a xylanase, a cellulase, an oxidoreductase; a phospholipase A1; a phospholipase A2; a phospholipase C; a phospholipase D; a galactolipase, a triacylglycerol lipase, an arabinofuranosidase, a transglutaminase, a pectinase, a pectate lyase, a protease, or any combination thereof. The enzyme combination may comprise the variant polypeptide of the present invention and a lipase, or the enzyme combination may comprise the variant polypeptide of the present invention, a lipase, and a xylanase.

The present invention is also directed to a composition comprising the variant polypeptide of the present invention.

The composition comprising the variant polypeptide of the present invention may also comprise a second enzyme.

Preferably the second enzyme is selected from the group consisting of: a second alpha-amylase, a lipase, a beta-amylase, a G4-amylase, a xylanase, a protease, a cellulase, a glucoamylase, an oxidoreductase, a phospholipase, and a cyclodextrin glucanotransferase.

The composition of the present invention may be used in the preparation of bakery products.

The present invention is also directed to a method of preparing a dough, the method comprising adding the variant polypeptide of the present invention to the dough.

"Dough" is defined as a mixture of flour, salt, yeast and water, which may be kneaded, molded, shaped or rolled prior to baking. In addition, also other ingredients such as sugar, margarine, egg, milk, etc. might be used. The term includes doughs used for the preparation of baked goods, such as bread, rolls, sandwich bread, baguette, ciabatta, croissants, sweet yeast doughs, etc.

The present invention is also directed to a method of preparing a baked product prepared from a dough, the method comprising adding the variant polypeptide of the present invention to the dough and baking the dough, thereby preparing the baked product.

The term "baked products" includes, but is not limited to, baked products such as bread, crispy rolls, sandwich bread, buns, baguette, ciabatta, croissants, noodles, as well as fine bakery wares like donuts, brioche, stollen, cakes, muffins, etc.

Baked products include, but are not limited to: bread, rolls, buns, pastries, cakes, flatbreads, pizza bread, pita bread, wafers, pie crusts, naan, lavish, pitta, focaccia, sourdoughs, noodles, cookies, doughnuts, deep-fried tortillas, pancakes, crepes, croutons, and biscuits. The baked product could also be an edible container such as a cup or a cone.

Baking bread generally involves mixing ingredients to form a dough, kneading, rising, shaping, baking, cooling and storage. The ingredients used for making the dough generally include flour, water, salt, yeast, and other food additives. In the method of the present invention the variant polypeptide of the present invention is one of the ingredients used for making the dough.

Flour is generally made from wheat and may be milled for different purposes such as making bread, pastries, cakes, biscuits pasta, and noodles. Alternatives to wheat flour include, but are not limited to: almond flour, coconut flour, chia flour, corn flour, barley flour, spelt flour, soya flour, hemp flour, potato flour, quinoa, teff flour, rye flour, amaranth flour, arrowroot flour, chick pea (garbanzo) flour, cashew flour, flax meal, macadamia flour, millet flour, sorghum flour, rice flour, tapioca flour, and any combination thereof. Flour type is known to vary between different regions and different countries around the world.

Treatment of flour or dough may include adding inorganic substances, organic substances such as fatty acids, carbohydrates, amino acids, proteins, and nuts. The flour or dough may be pretreated prior to baking by cooling, heating, irradiation, agglomeration, or freeze-drying. In addition, the flour or dough may be pretreated prior to baking by adding enzymes such as the variant polypeptide of the present invention, or micro-organisms, such as yeasts.

Yeast breaks down sugars into carbon dioxide and water. A variety of Baker's yeast, which are usually derived from *Saccharomyces cerevisiae*, are known to those skilled in the art including, but not limited to: cream yeast, compressed yeast, cake yeast, active dry yeast, instant yeast, osmotolerant yeasts, rapid-rise yeast, deactivated yeast. Other kinds of yeast include nutritional yeast, brewer's yeast, distiller's and wine yeast.

Sweeteners which can be added to the dough include, but are not limited to: liquid sugar, syrups, white (granulated) sugars, brown (raw) sugars, honey, fructose, dextrose, glucose, high fructose corn syrup, molasses, stevia and artificial sweeteners.

Emulsifiers which can be added to the dough include, but are not limited to, diacetyl tartaric acid esters of monoglycerides (DATEM), sodium stearoyl lactylate (SSL), calcium stearoyl lactylate (CSL), ethoxylated mono- and diglycerides (EMG), polysorbates (PS), and succinylated monoglycerides (SMG).

Other food additives which may be used in the methods of baking include: lipids, oils, butter, margarine, shortening, butterfat, glycerol, eggs, diary, non-diary alternatives, thickeners, preservatives, colorants, and enzymes.

Ingredients or additives for baking may be added individually to the dough during the baking process. The ingredients or additives may also be combined with more than one ingredient or additive to form pre-mixes and then the pre-mixes are added to the dough during the baking process. The flour or dough mixtures may be prepared prior to baking including ready—for oven doughs, packaged doughs or packaged batters.

Bakery products may be modified to meet special dietary requirements such as sugar-free diet, gluten-free diet, low fat diet, or any combination thereof. The enzymes may extend shelf-life of a dough-based product or provide antimicrobial (mold-free) effects.

"Bread volume" is the volume of a baked good determined by using a laser scanner (e.g. Volscan Profiler ex Micro Stable System) to measure the volume as well as the specific volume. The term also includes the volume which is determined by measuring the length, the width and the height of certain baked goods.

The use of the variant polypeptide of the present invention in a method of making a dough increases the resilience of the baked product prepared from the dough. The baked product may be stored for five days, 10 days, 15 days or 20 days, before resilience is determined. The resilience can be determined by a texture analyzer test using the Texture Profile Analysis (TPA). The TPA is a two cycle compression test and the resilience is calculated by Recoverable work done divided by hardness work done by the texture analyzer. The resilience of a baked product prepared from dough using the variant polypeptide of the present invention is increased by at least 5% or 8%, preferably by at least 10% or 12%, more preferably by at least 15% or 20% and most preferably by at least 25% or 30%.

The use of the variant polypeptide of the present invention in a method of making a dough decreases the hardness of the baked product prepared from the dough after storage. Typically, the baked product is stored for 10 days, 15 days or 20 days at room temperature, before the hardness is determined. The hardness may be determined according to the AACC 74-09 test, for example using a 35 mm sample and 5 kg load cell. The following parameters may be used in the test: Pre-test speed: 1 mm/sec, Test speed: 5 mm/sec, Post-Test speed: 5 mm/sec, Target Mode: Distance, Distance: 10 mm, Time 5 sec, Trigger Type: Auto (Force), Trigger Force: 5 g. The hardness of a baked product prepared from dough using the variant polypeptide of the present invention is decreased by at least 5% or 8%, preferably by at least 10% or 12%, more preferably by at least 15% or 20% and most preferably by at least 25% or 30%.

The variant polypeptide of the present invention may be useful for other industrial applications. The variant polypeptide having alpha-amylase enzyme activity may be used in a detergent, a personal care product, in the processing of textiles, in pulp and paper processing, in the production of ethanol, lignocellulosic ethanol, or syrups; or as viscosity breakers in oilfield and mining industries.

The following examples are provided for illustrative purposes. It is thus understood that the examples are not to be construed as limiting. The skilled person will clearly be able to envisage further modifications of the principles laid out herein.

EXAMPLES

Example 1: Generation of Variant Alpha-Amylase Enzymes

The parent enzyme according to SEQ ID No. 1, which is encoded by the nucleic acid sequence of SEQ ID No.:2. The parent enzyme was engineered in the lab to generate non-naturally occurring alpha-amylase variant enzymes having an increased exoamylase activity compared to the parent enzyme. The variant polypeptide enzymes were created starting with the parent enzyme and evolving it using Gene Site Saturation Mutagenesis (GSSM) of the parent enzyme as described in at least U.S. Pat. Nos. 6,562,594, 6,171,820, and 6,764,835; Error Prone PCR; and/or Tailored Multi-Site-Combinatorial Assembly (TMSCA), as described in U.S. Pat. No. 9,476,078.

Variant polypeptides having one amino acid substitution compared to the parent polypeptide according to SEQ ID No. 1 were generated and tested for alpha-amylase activity using the PAHBAH and iodine assays. All data points were normalized by subtracting the plate background from all sample data points.

A negative linear trend or correlation was observed between the Iodine assay which detects the amount of starch and the PAHBAH assay which detects reducing ends. In other words, reducing ends are more prominent when there is less starch available at the end of the assay. A linear regression on sample data points was applied in order to predict the line that describes the negative correlation. To find improved mutants having an increased exoamylase activity compared to the parent enzyme, mutations that break this linear trend were identified. Mathematically, these mutations were selected by constructing a 90% confidence band around the linear regression line and mutations that are above the upper limit of the 90% confidence band (threshold) were picked. An exemplary graph demonstrating the linear regression is shown in FIG. 1. Table 1 below shows different single mutants which have a positive distance to the upper threshold, i.e. the 90% confidence band and which were therefore considered as mutants with an increased exoamylase activity. Further mutants were selected manually in view of secondary indicia such as results in mass spectrometry.

Table 1

TABLE 1

| Mutant | Mutation | PAHBAH | Iodine | Threshold | Distance to threshold |
|---|---|---|---|---|---|
| 0 | Q32R | 0.183 | 1.674 | 0.133 | 0.05 |
| 1 | A433W | 0.748 | 1.587 | 0.746 | 0.002 |
| 2 | N257R | 0.449 | 1.815 | 0.438 | 0.011 |
| 3 | D256A | 0.195 | 2.073 | 0.17 | 0.025 |
| 4 | I45M | 0.407 | 1.926 | 0.394 | 0.013 |
| 5 | Y236H | 0.395 | 1.876 | 0.377 | 0.018 |
| 6 | F197K | 0.336 | 1.516 | 0.306 | 0.03 |
| 7 | W26G | 1.078 | 1.713 | 1.061 | 0.017 |
| 8 | G160E | 0.486 | 2 | 0.48 | 0.006 |
| 9 | W234C | 0.042 | 1.973 | −0.011 | 0.053 |
| 10 | V90G | 1.216 | 1.029 | 1.272 | −0.056 |
| 11 | V435S | 0.393 | 1.766 | 0.389 | 0.004 |
| 12 | A96T | 0.198 | 2.054 | 0.154 | 0.044 |
| 13 | F243K | 0.267 | 2.048 | 0.233 | 0.034 |
| 14 | T258C | 0.359 | 1.919 | 0.31 | 0.049 |
| 15 | E88Y | 0.471 | 1.899 | 0.452 | 0.019 |
| 16 | F197A | 0.254 | 1.657 | 0.237 | 0.017 |
| 17 | G160V | 0.655 | 1.704 | 0.218 | 0.437 |
| 18 | G22Q | 0.847 | 1.86 | 0.756 | 0.091 |
| 19 | K152M | 0.207 | 1.904 | 0.218 | −0.011 |
| 20 | P35K | 0.398 | 2.147 | | |
| 21 | K76R | 0.397 | 2.111 | 0.251 | 0.146 |
| 22 | N91T | 0.476 | 1.87 | 0.41 | 0.066 |
| 23 | P261F | 0.284 | 1.951 | 0.264 | 0.02 |
| 24 | F68P | 0.417 | 1.954 | 0.395 | 0.022 |
| 25 | P261C | 0.161 | 2.051 | 0.144 | 0.017 |
| 26 | W175N | 0.318 | 1.228 | 0.303 | 0.015 |
| 27 | S4T | 0.342 | 2.175 | 0.329 | 0.013 |
| 28 | V311L | 0.218 | 2.043 | 0.166 | 0.052 |
| 29 | R82N | 1.232 | 1.515 | 0.959 | 0.273 |
| 30 | W128Y | 0.342 | 1.951 | 0.327 | 0.015 |
| 31 | L117R | 0.309 | 1.985 | 0.307 | 0.002 |
| 32 | I25W | 0.493 | 2.052 | 0.46 | 0.033 |
| 33 | Y126V | 0.485 | 1.625 | 0.486 | −0.001 |
| 34 | T29G | 1.788 | 1.992 | 1.128 | 0.66 |
| 35 | V90M | 0.986 | 1.264 | 0.989 | −0.003 |
| 36 | P21W | 0.997 | 1.763 | 0.928 | 0.069 |
| 37 | P21E | 0.437 | 1.603 | 0.428 | 0.009 |
| 38 | N380L | 0.521 | 1.726 | 0.489 | 0.032 |
| 39 | G416Q | 0.271 | 1.895 | 0.264 | 0.007 |
| 40 | W128Y, A141T | 0.389 | 1.91 | 0.373 | 0.016 |
| 41 | F243T | 0.364 | 1.923 | 0.36 | 0.004 |
| 42 | G53A | 0.155 | 1.845 | 0.221 | −0.066 |
| 43 | S59P | 0.29 | 2.066 | 0.322 | −0.032 |
| 44 | F243A | 0.194 | 2.107 | 0.174 | 0.02 |
| 45 | I292E | 0.3 | 1.953 | 0.231 | 0.069 |
| 46 | I292A | 0.183 | 1.801 | 0.192 | −0.009 |
| 47 | G423M | 0.344 | 2 | 0.316 | 0.028 |
| 48 | V200S | 0.051 | 2.052 | 0.047 | 0.004 |
| 49 | V134A | 0.24 | 1.937 | 0.237 | 0.003 |
| 50 | K2H | 1.437 | 0.651 | 1.351 | 0.086 |
| 51 | Y3R | 2.492 | 0.713 | 2.484 | 0.008 |
| 52 | A105W | 0.329 | 1.772 | 0.338 | −0.009 |
| 53 | G270Y | 0.851 | 0.84 | 1.278 | −1.134 |
| 54 | V264R | 0.113 | 2.135 | 0.106 | 0.007 |

The following variant polypeptides having a combination of amino acid substitutions compared to the parent polypeptide according to SEQ ID No. 1 were generated and tested for alpha-amylase activity using the PAH BAH and Iodine assays.

TABLE 2

| Enzyme No. | Mutation | PAHBAH | Iodine |
|---|---|---|---|
| 40 | W128Y, A141T | | |
| 55 | 22Q-35K-59P-128Y-256A | 0.52525 | 1.966 |
| 56 | 22Q-128Y-175N-200S-433W | 1.1055 | 1.75225 |
| 57 | 22Q-35K-59P-256A | 0.81525 | 1.8835 |
| 58 | 22Q-175N-200S-256A-433W | 1.269 | 1.947 |
| 59 | 128Y-175N-256A | 2.090 | 1.160 |
| 60 | 22Q-59P-200S-256A-433W | 1.565 | 1.512 |
| 61 | 22Q-175N-200S-256A | 2.576 | 0.915 |
| 62 | 22Q-59P | 1.282 | 1.745 |
| 63 | 22Q-35K-128Y-175N-200S-256A-433W | 0.993 | 1.848 |
| 64 | 22Q-35K-59P-128Y-433W | 0.776 | 1.978 |
| 65 | 22Q-128Y-175N-256A | 0.932 | 1.867 |
| 66 | 35K-128Y-200S-256A | 1.850 | 1.517 |
| 67 | 22Q-59P-175N-200S-433W | 1.214 | 1.786 |
| 68 | 22Q-59P-128Y-200S-433W | 1.013 | 1.775 |
| 69 | 22Q-59P-175N-200S-256A-433W | 3.236 | 1.290 |
| 70 | 22Q-59P-128Y-256A | 1.272 | 1.584 |
| 71 | 59P-200S-256A-433W | 1.318 | 1.647 |
| 72 | 35K-59P-128Y-175N-200S-256A-433W | 0.642 | 1.980 |
| 73 | 22Q-59P-128Y-256A-433W | 0.665 | 1.961 |
| 74 | 22Q-59P-128Y-175N-200S-433W | 0.806 | 1.959 |
| 75 | 22Q-128Y-175N-433W | 1.154 | 1.765 |
| 76 | 59P-128Y-200S | 0.942 | 1.837 |
| 77 | 35K-59P-200S-433W | 0.812 | 1.825 |
| 78 | 59P-128Y-200S-256A | 0.850 | 1.743 |
| 79 | 59P-128Y-200S-433W | 0.810 | 1.773 |
| 80 | 128Y-200S-433W | 0.898 | 1.669 |

Example 2: Expression of Variant Alpha-Amylases

The variant polypeptides having alpha-amylase activity were obtained by constructing expression plasmids containing the encoding polynucleotide sequences, transforming said plasmids into *Pichia pastoris* (*Komagataella phaffii*) and growing the resulting expression strains in the following way.

Fresh *Pichia pastoris* cells of the expression strains were obtained by spreading the glycerol stocks of sequence-confirmed strains onto Yeast extract Peptone Dextrose (YPD) agar plates containing Zeocin. After 2 days, starter seed cultures of the production strains were inoculated into 100 mL of Buffered Glycerol complex Medium (BMGY) using cells from these plates, and grown for 20-24 hours at 30° C. and 225-250 rpm. Seed cultures were scaled up by transferring suitable amounts into 2-4 L of BMMY medium in a baffled Fermenter. Fermentations were carried out at 30° C. and under 1100 rpm of agitation, supplied via flat-blade impellers, for 48-72 hours. After the initial batch-phase of fermentation, sterile-filtered methanol was added as feed whenever the dissolved oxygen level in the culture dipped below 30%. Alternatively, feed was added every 3 hours at 0.5% v/v of the starting batch culture. The final fermentation broth was centrifuged at 7000×g for 30 mins at 4° C. to obtain the cell-free supernatant.

The variant polypeptides having alpha-amylase activity were detected by assaying the supernatant for protein of interest expression by either SDS-PAGE or capillary electrophoresis.

Example 3: PAHBAH Assay

Quantitation of starch hydrolysis for the alpha-amylase and variant enzymes was measured using the 4-Hydroxybenzhydrazide method as described in Lever M. (1972) Anal. Biochem. 47, 273-279, with the following modifications. 112 μL of 1% potato amylopectin was reacted with 12.5 μL of diluted enzyme at 65° C. and samples taken at 60 minutes. The reaction was then quenched by mixing into 100 μl 1% PAHBAH reagent. The reaction was heated to 95° C. for 6 minutes, cooled to room temperature, and the solution absorption was read at 410 nm in a BioTek plate reader.

Example 4: Iodine Assay

The extent of amylopectin degradation was assessed by staining amylopectin with Lugol reagent. After incubation of the enzyme sample with 1% amylopectin at 65° C. for 1 hour, the sample was diluted to 10% with Lugol solution at room temperature. The absorbance was read at 550 nm in a BioTek plate reader.

Example 5: Iodine Vs PAHBAH Value

The iodine value per enzymatic reaction was used as a measure of amylopectin degradation. Thus, mutants were selected based on having a high iodine value and/or high hydrolysis activity as measured by the PAHBAH value. Evolution of the alpha amylase based on these parameters generated an enzyme whose activity was shifted from a sharp endoamylase activity to more exoamylase activity. This is indicated by a higher iodine value for a given PAHBAH value as compared to the parent enzyme (see FIG. 1).

Example 6: BCA Assay

Quantitation of starch hydrolysis for the alpha-amylase and variant enzymes was measured using the BCA Reducing Ends Assay. Briefly, 1 part Copper (II) Sulfate Solution with 49 parts Bicinchoninic acid solution was mixed prior to the start of the assay. 1% potato amylopectin was used as a substrate and kept at the assay temperature for 10 minutes prior to the addition of enzyme.

112 μL of 1% potato amylopectin was reacted with 12.5 μL of diluted enzyme at temperatures between 50° C. and 80° C. and 10 μL samples were taken at equal time intervals within 10 minutes. The reaction samples were immediately quenched by mixing into 100 ul BCA reagent and heated to 80° C. for 30 minutes, cooled to room temperature, and the solution absorption was read at 560 nm in a BioTek plate reader. Experimental slopes were correlated to a glucose standard to generate specific activities. The following table 3 shows the activity in the BCA assay of the mutants shown in table 1 in μmoles/min/mg enzyme (PI) at different temperatures.

TABLE 3

| Mutant | 50° C. | 60° C. | 70° C. | 80° C. |
|---|---|---|---|---|
| 30 | 286.08 | 449.71 | 436.65 | 751.3 |
| 48 | 613.23 | 952.11 | 1330.73 | 1350.43 |
| 3 | 283.03 | 372.88 | 561.72 | 502.69 |
| 1 | 286.26 | 453.85 | 648.42 | 680.25 |
| 26 | 434.75 | 511.41 | 666.77 | 677.08 |
| 29 | 515.93 | 832.56 | 879.57 | 1309.88 |
| 43 | 257.56 | 376.44 | 502.05 | 591.92 |
| 18 | 24.81 | 39.9 | 50.52 | 56.34 |
| 38 | 297.09 | 494.02 | 668.19 | 734.43 |
| 41 | 265.66 | 416.16 | 599.74 | 749.78 |
| 23 | 635.53 | 902.18 | 1286.00 | 1144.53 |
| 44 | 205.00 | 284.19 | 292.75 | 388.67 |
| 47 | 671.89 | 1007.43 | 1491.99 | 1424.00 |
| 39 | 404.70 | 605.80 | 816.99 | 753.32 |
| Parent enzyme SEQ ID NO: 1/2 | 549.24 | 785.92 | 989.15 | 1228.22 |

Example 7: Baking Performance of the Variant Alpha-Amylases

The baking performance of the variant polypeptides having alpha-amylase activity was tested in wheat pan bread produced in a straight process. The bread dough was prepared by mixing 1000 g of flour type 550 (Vogtmühlen Illertissen), 30 g compressed yeast, 20 g salt, 20 g sugar, 20 g margarine, 60 ppm ascorbic acid, 150 ppm Nutrilife® CS 30 (fungal xylanase, cellulase, fungal alpha-amylase), 8 g Nutrisoft® 55 (distilled monoglyceride) and 600 g water in a Kemper SP 15 spiral mixer for 4.5 minutes at speed 1 and 2.5 minutes at speed 2, to a final dough temperature of 28° C. After a resting of 15 minutes, the dough was divided into 500 g pieces, rounded and proofed for 15 minutes. Afterwards the dough pieces were molded, given into a baking tin and proofed for 80 minutes at 35° C. at relative humidity of 85%. The proofed dough pieces were baked in a deck oven for 25 minutes at 255° C./240° C. under lower and upper heat, with 15 seconds steam injection.

Figure 3:
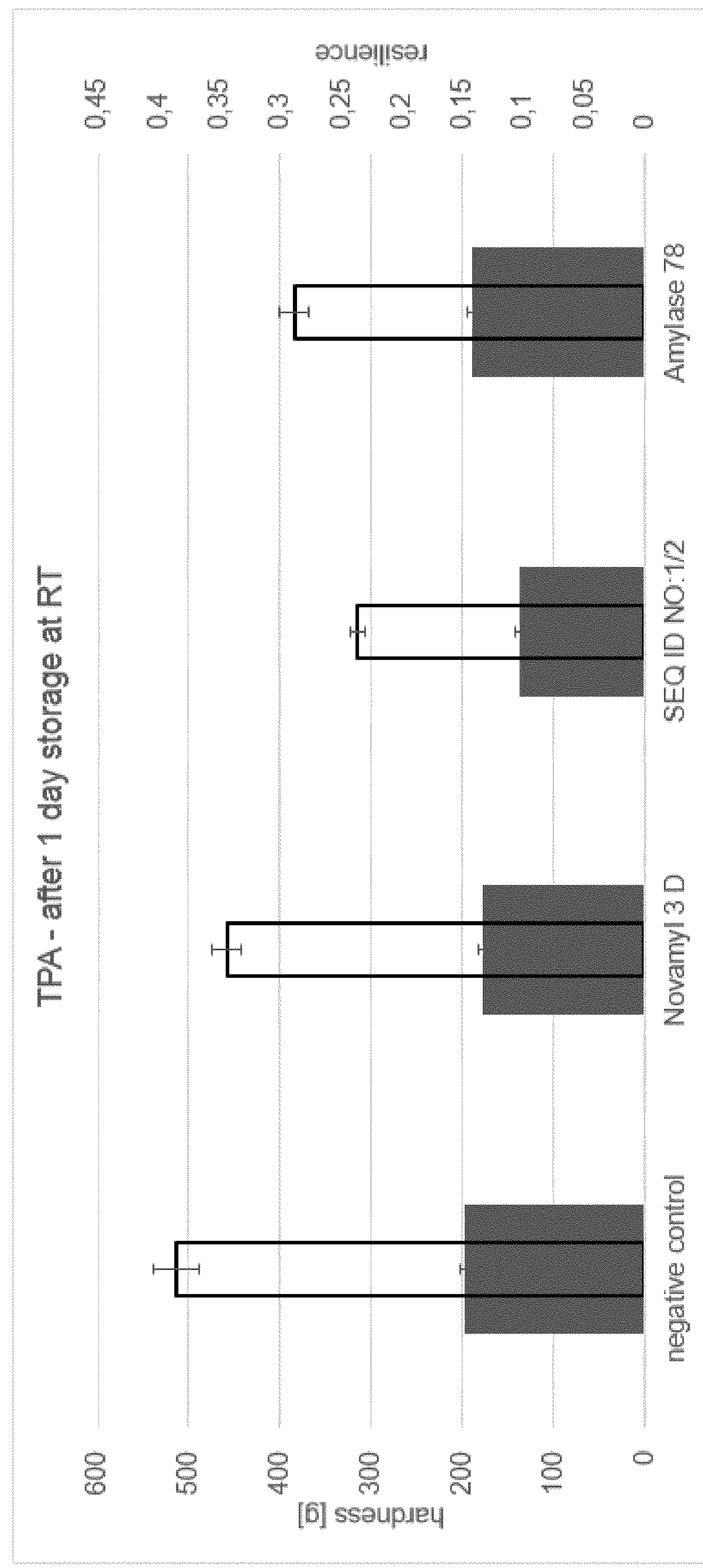
FIG. 3: Texture profile Analysis (TPA)—after 1 day storage at room temperature (RT), hardness, and resilience, for a negative control (no enzyme), Novamyl 3D, SEQ ID NO:1/2, and Enzyme 78.

The variant polypeptide enzyme samples were added to the flour at dosages from 27 ppm to 325 ppm. The effects on the dough properties and on the final baked goods were compared to a negative control (no enzyme), and to Novamyl 3D®. The results were measured for hardness and resilience and are shown in FIG. 3.

The volume effect was determined by measuring the bread loafs via a laser scanner (Stable Micro Systems VolScan Profiler, VolScan 600). The negative control is defined as 0%.

Dough properties were evaluated haptically by a skilled master baker and described in comparison to the negative control.

The ready baked breads were packed and sealed in a plastic bag. In addition, they partly were pasteurized for 90 minutes at 85° C. The crumb properties were determined on freshly baked bread and after defined storage times, typically after 1, 10, 20 days, was determined by texture profile analyses using a texture analyzer (Stable Micro Systems, TA.XTplus Texture Analyzer). Therefore, 25-millimeter-thick slices were cut out of the middle of the bread loafs, prior to the measurement.

What is claimed is:

1. A variant polypeptide of the alpha-amylase according to SEQ ID No. 1, comprising an amino acid sequence which is at least 90% identical to the sequence according to SEQ ID No. 1 and having alpha-amylase activity, wherein the variant polypeptide has an increased exoamylase activity compared to the alpha-amylase according to SEQ ID No. 1, wherein the variant comprises at least one amino acid modification compared to the amino acid sequence according to SEQ ID No. 1 and wherein the at least one amino acid modification is an amino acid substitution selected from the group consisting of: K2H, Y3R, S4T, P21E, P21W, G22Q, 125W, W26G, T29G, Q32R, P35K, 145M, G53A, S59P, F68P, K76R, R82N, E88Y, V90G, V90M, N91T, A96T, A105W, L117R, Y126V, W128Y, V134A, A141T, K152M, G160E, G160V, W175N, F197A, F197K, V200S, W234C, Y236H, F243A, F243K, F243T, D256A, N257R, T258C, P261C, P261F, V264R, G270Y, 1292A, I292E, V311L, N380L, G416Q, G423M, A433W, and V435S in the numbering of SEQ ID No. 1.

2. The variant polypeptide of claim 1, wherein the variant polypeptide comprises a combination of amino acid modifications compared to the amino acid sequence according to SEQ ID No. 1.

3. The variant polypeptide of claim 2, wherein the combination of amino acid modifications is a combination of amino acid substitutions which is selected from the group consisting of:

(a) G22Q, P35K, S59P, W128Y, D256A;
(b) G22Q, W128Y, W175N, V200S, A433W;
(c) G22Q, P35K, S59P, D256A;
(d) G22Q, W175N, V200S, D256A, A433W;
(e) W128Y, W175N, D256A;
(f) G22Q, S59P, V200S, D256A, A433W;
(g) G22Q, W175N, V200S, D256A;
(h) G22Q, S59P;
(i) G22Q, P35K, W128Y, W175N, V200S, D256A, A433W;
(j) G22Q, P35K, S59P, W128Y, A433W;
(k) G22Q, W128Y, W175N, D256A;
(l) P35K, W128Y, V200S, D256A;
(m) G22Q, S59P, W175N, V200S, A433W;
(n) G22Q, S59P, W128Y, V200S, A433W;
(o) G22Q, S59P, W175N, V200S, D256A, A433W;
(p) G22Q, S59P, W128Y, D256A;
(q) S59P, V200S, D256A, A433W;
(r) P35K, S59P, W128Y, W175N, V200S, D256A, A433W;
(s) G22Q, S59P, W128Y, D256A, A433W;
(t) G22Q, S59P, W128Y, W175N, V200S, 433W;
(u) G22Q, W128Y, W175N, A433W;
(v) S59P, W128Y, V200S;
(w) P35K, S59P, V200S, A433W;
(x) S59P, W128Y, V200S, D256A;
(y) S59P, W128Y, V200S, A433W; and
(z) W128Y, V200S, A433W in the numbering of SEQ ID No. 1.

4. The variant polypeptide according to claim 1, wherein the variant polypeptide is a fragment of the full length amino acid sequence according to SEQ ID No. 1.

5. A variant polypeptide comprising a hybrid of at least one variant polypeptide according to claim 1, and a second polypeptide having amylase activity, wherein the hybrid has alpha-amylase activity.

6. A composition comprising the variant polypeptide according to claim 1.

7. The composition according to claim 6, further comprising a second enzyme.

8. The composition according to claim 7, wherein the second enzyme is selected from the group consisting of: a second alpha-amylase, a lipase, a beta-amylase, a G4-amylase, a xylanase, a protease, a cellulase, a glucoamylase, an oxidoreductase, a phospholipase, and a cyclodextrin glucanotransferase.

9. A method of making a variant polypeptide comprising: providing a template nucleic acid sequence encoding the polypeptide variant according to claim 1, transforming the template nucleic acid sequence into an expression host, cultivating the expression host to produce the variant polypeptide, and purifying the variant polypeptide.

10. The method of claim 9, wherein the template nucleic acid is a variant nucleic acid sequence of the nucleic acid sequence as set forth in SEQ ID NO. 2, wherein the variant nucleic acid sequence is a nucleic acid sequence that is at least 90% identical to the nucleic acid sequence as set forth in SEQ ID No. 2, wherein the variant nucleic acid sequence encodes a polypeptide having alpha-amylase activity and having an increased exoamylase activity compared to the alpha-amylase encoded by the nucleic acid sequence according to SEQ ID No.2.

11. A method of preparing a dough or a baked product prepared from the dough, the method comprising adding a variant polypeptide according to claim 1 to the dough and eventually baking the dough.

12. The composition of claim 6, wherein the composition is used for processing starch, for cleaning or washing textiles, hard surfaces, or dishes, for making ethanol, for treating an oil well, for processing pulp or paper, for feeding an animal or for making syrup.

* * * * *